(12) United States Patent
von Meyer

(10) Patent No.: US 7,047,832 B1
(45) Date of Patent: May 23, 2006

(54) APPARATUS FOR MEASURING GAS EXCHANGE

(75) Inventor: William von Meyer, Pendleton, SC (US)

(73) Assignee: Oporgenics, Inc., LLC, Pendleton, SC (US)

( * ) Notice: Subject to any disclaimer, the term of this patent is extended or adjusted under 35 U.S.C. 154(b) by 14 days.

(21) Appl. No.: 10/983,873

(22) Filed: Nov. 8, 2004

(51) Int. Cl.
  *G05D 9/00* (2006.01)
  *G05D 16/00* (2006.01)
  *B01L 3/00* (2006.01)

(52) U.S. Cl. .................. 73/900; 422/102; 422/106; 422/109

(58) Field of Classification Search ............. 73/900, 73/747, 736
  See application file for complete search history.

(56) References Cited

U.S. PATENT DOCUMENTS

| | | | |
|---|---|---|---|
| 383,433 A | 5/1888 | Bonte | |
| 940,258 A | 11/1909 | Kiely | |
| 1,834,536 A | 12/1931 | Schaut | 73/426 |
| 2,268,154 A | 12/1941 | Kelm | 73/747 |
| 3,023,622 A | 3/1962 | Hezarifend | 73/747 |
| 3,150,524 A | 9/1964 | Arens | 73/747 |
| 3,720,201 A | 3/1973 | Ramsey, III | 600/561 |
| 3,868,224 A | 2/1975 | Davis | 422/82.05 |
| 3,890,842 A | 6/1975 | Ramsey, III | 73/731 |
| 3,901,083 A | 8/1975 | Wallace | 73/715 |
| 3,903,745 A | 9/1975 | Bolser | 73/863.21 |
| 3,921,455 A | 11/1975 | Staubli | 73/741 |
| 3,938,393 A | 2/1976 | Mogensen | 73/431 |
| 3,949,484 A | 4/1976 | Cluley | 33/367 |
| 4,023,416 A | 5/1977 | Ormsby | 73/744 |
| 4,136,560 A | 1/1979 | Gellos | 73/146.8 |
| 4,263,405 A | 4/1981 | Melnick | 435/287.5 |
| 4,282,881 A | 8/1981 | Todd | 600/487 |
| 4,314,029 A | 2/1982 | Ohtake | 435/287.5 |
| 4,399,809 A | 8/1983 | Baro | 600/31 |
| 4,509,267 A | 4/1985 | Flaten | 33/644 |
| 4,535,634 A | 8/1985 | Troutman, Jr. | 73/747 |
| 4,727,887 A | 3/1988 | Haber | 600/561 |
| 4,779,464 A | 10/1988 | Schwien | 73/708 |
| 4,785,669 A | 11/1988 | Benson | 73/718 |
| 6,133,041 A * | 10/2000 | Park | 436/121 |

* cited by examiner

*Primary Examiner*—Hezron Williams
*Assistant Examiner*—Tamiko Bellamy
(74) *Attorney, Agent, or Firm*—McNair Law Firm, P.A.

(57) ABSTRACT

A container having a port for holding a liquid medium and a reactant that interact to produce a change in gas levels within the container. A removable stopper for insertion into the port creating an airtight seal. A tube extending through the stopper into the container having a distal end for being submerged in the liquid medium for receiving the liquid medium and monitoring a change in the level of the liquid medium within the container. A controller is provided extending through the stopper into the container for setting the liquid medium at a level within the tube, wherein the controller is operable to direct the liquid medium into the tube to a desired level so that a change in gas levels caused by the interaction of the reactant with the liquid medium can be monitored through a change in the level of the liquid medium within the tube.

24 Claims, 2 Drawing Sheets

APPARATUS FOR MEASURING GAS EXCHANGE

BACKGROUND OF THE INVENTION

1) Field of the Invention

The present invention relates to manometers, and more particularly, to a durable, economical, high volume, high precision manometer which can easily be operated and taught in a classroom setting, is leaks resistant, disposable at low cost if employed for handling radio active solid substrates, and which allows for the manometer to be reset without exposing the interior of the apparatus to external ambient air.

2) Description of Related Art

The prior art is replete with various devices for measuring pressure differentials on a liquid medium caused by gas exchange. However, the vast majority of these devices that attempt to provide accurate high precision results are extremely expensive to manufacture, fragile, and difficult to operate without leaks, even for experienced lab technicians. Further, digital gas measurement devices do not permit students to see the gas produced in many cases, as it is often detected in solution in a fluid environment. Digital sensors also have the disadvantage of a useful life of 18 to 24 months due to wear of the probe materials, requiring schools to reinvest in the expensive detection device or risk classroom downtime.

The quantitative instruction of students about catalase reactions and respiration in an average classroom or school laboratory setting has been frustrated by the cost of equipment, complexity of the equipment and consequential gleaning of data. Importantly, the matching of substrates to equipment size must be such that a reaction can be set up and data determined within the class time period available. At the present time, the most common means of examination of gas exchange or production reactions would be conducted in what is termed a Warburg apparatus.

The Warburg apparatus is a complex manometer. It employs an expensive flask of small size immersed in a fluid bath of constant temperature. The constant temperature is employed so that comparisons can be made between flasks employing very small volumes of gas expired from tissues, which is measured in microliters. The initial cost of the fluid incubator, agitator set-up, manometer tubes, and fitted glassware for three trial samples is approximately $2000, or more. It has been stated by the American Society of Microbiologists (*Manual of Methods for General Bacteriology*, pg. 325, section 16.6, Manometry) that manometry is essentially a research matter threatening to become a "lost art" due to an insufficiency of time to teach proficiency with such apparatus as a Warburg manometer.

During set up of a Warburg apparatus, what is know as a flask constant would require determination using mercury or a defined fluid. This is done in a Warburg situation because the amount of gas which could dissolve in the fluid of a Warburg is large in proportion to the space available. The Warburg output values are generally measured in microliters. For fast reactions such as the reaction of peroxide with a few grams of tissue or seeds, as would be used in a classroom environment, the Warburg capacity to measure output gas is used up rapidly since tissue gas output from peroxide can be in milliliters per minute rather than microliters per minute. The Warburg often requires frequent resetting of the manometer to release excess gas and reset the apparatus for further experimentation. When several manometers are running at once in a Warburg bath under fast reaction conditions, the resetting times for each manometer can become excessive and overly burdensome, particularly in a student circumstance. This also demands the manometers in line be reset to avoid running over their capacity, and ruining the experiments being conducted. The matching of tissue volume and substrate in the Warburg apparatus has become a tedium causing it to be employed mainly as a research tool. Further, leaks caused by the multitude of connections to tubes and flasks in such apparatus have been a major source of frustration in obtaining consistent accurate results in measurement.

For the student experiencing manometry for the first time, the tedium of loading, sealing off leaks, and finding the constants involved in using a Warburg apparatus are overwhelming and take far too long for a single class period. It takes considerable time to get accomplished with the apparatus and the limited volume of the Warburg essentially makes it useless for conducting the type of vigorous reactions that can provide students with useful results in a single class time period.

SUMMARY OF THE INVENTION

The present invention includes a container for holding a liquid medium and a reactant that interacts with the liquid medium to produce a change in gas levels within the container. The container including a port for accessing an interior of the container. A removable stopper is provided for insertion into the port creating an airtight seal. A tube is provided extending through the stopper into the container having a distal end for being submerged in the liquid medium. The tube is adapted for receiving the liquid medium and monitoring a change in the level of the liquid medium within the container as a result of gas exchange. A controller is provided extending through the stopper into the container for setting the liquid medium at a level within the tube, wherein the controller is operable to direct the liquid medium into the tube to a desired level so that a change in gas levels caused by the interaction of the reactant with the liquid medium can be monitored through a change in the level of the liquid medium within the tube.

In a further embodiment, the container comprises a bottle composed of material selected from the group consisting of polymeric plastic and glass, and wherein the container includes a narrowed neck portion having a constant diameter forming the port. The bottle includes approximately a 200 cc capacity for receiving the liquid medium, and a port adapted to receive at least a #7 size rubber stopper.

In a further embodiment, the removable stopper comprises a solid rubber stopper which includes a first hole extending through the stopper for receiving the tube in an airtight arrangement, and a second hole extending through the stopper for receiving the controller in an airtight arrangement. A gas impermeable sealant may be disposed in the first hole and the second hole for creating an airtight seal between the stopper, the tube, and the controller.

In a further embodiment, the tube includes graduated indicia for gauging a change in the liquid medium level within the tube.

In a further embodiment, the tube is comprised of a shatter resistant material selected from the group consisting of acrylic and carbonate polymer.

In a further embodiment, the tube is approximately 44 cm to 56 cm in length with an external diameter of approximately ¼" to 5/16" for receiving the liquid medium.

In a further embodiment, the distal end of the tube is positioned approximately ½ cm from a bottom of the container, and the container is adapted for submerging the distal end of the tube in at least 1 cm of liquid medium.

In a further embodiment, a stand is included which is adapted for holding the manometer in a generally upright orientation which includes a graduated backing parallel with the tube for gauging a change in the level of the liquid medium within the tube.

In a further embodiment, the controller includes a graduated reservoir mounted outside the container, a conduit passing through the stopper in an airtight arrangement into the container to interconnect the graduated reservoir and container in fluid communication, and a movable plunger mounted in the graduated reservoir, whereby movement of the plunger forces a fluid medium to be injected into the container or withdrawn into the graduated reservoir to result in a change in the level of liquid medium in the container and thereby the level of liquid medium in the tube, which allows the level of liquid medium in the tube to be adjusted and reset during a testing procedure without exposing an interior of the container to ambient air.

In a further embodiment, the graduated reservoir has approximately a 10 cc to 25 cc capacity for containing the fluid medium. The fluid medium may be a gas or a liquid.

In a further embodiment, the liquid medium comprises a peroxide.

In a further embodiment, the reactant is selected from the group consisting of soil, seeds, salts, food stuffs, and living tissue which reacts with the liquid medium.

A method for measuring gas exchange is also disclosed herein which comprises the steps of: providing a container having an open port for accessing the container; inserting a liquid medium into the container; inserting a reactant into the container for interacting with the liquid medium to produce a change in gas levels within the container; providing a removable stopper carrying an elongated tube and a controller for insertion into the port creating an airtight seal; inserting the stopper carrying the tube and the controller into the port so that a distal end of the tube is submerged in the liquid medium and the controller is in fluid communication with the container; and, operating the controller to direct the liquid medium into the tube to set the liquid medium at a desired level within the tube so that a change in gas levels within the container caused by the interaction of the reactant with the liquid medium results in a change in the liquid medium level within the tube to indicate gas exchange.

In a further embodiment, the method includes the steps of providing a control container having an open port and inserting a control medium into the container.

In a further embodiment, the method includes the step of bringing both the liquid medium and the control medium into equilibrium with room temperature. In practice, this is done before a test is run.

In a further embodiment, the method includes the steps of providing a second stopper carrying an elongated tube and a controller, and inserting the second stopper into the port of the control container in an airtight arrangement so that a distal end of the tube is submerged in the control medium and the controller is in fluid communication with the control container.

In a further embodiment, the method includes the step of operating the controller of the control container to direct the control medium into the tube to set the control medium at a desired starting level within the tube so that a change in room temperature results in a change in the level of control medium within the tube of the control container, whereby a change in room temperature can be accounted for in accurately measuring gas exchange between the liquid medium and the reactant.

BRIEF DESCRIPTION OF THE DRAWINGS

The construction designed to carry out the invention will hereinafter be described, together with other features thereof. The invention will be more readily understood from a reading of the following specification and by reference to the accompanying drawings forming a part thereof, wherein an example of the invention is shown and wherein.

DETAILED DESCRIPTION

Figure 1:
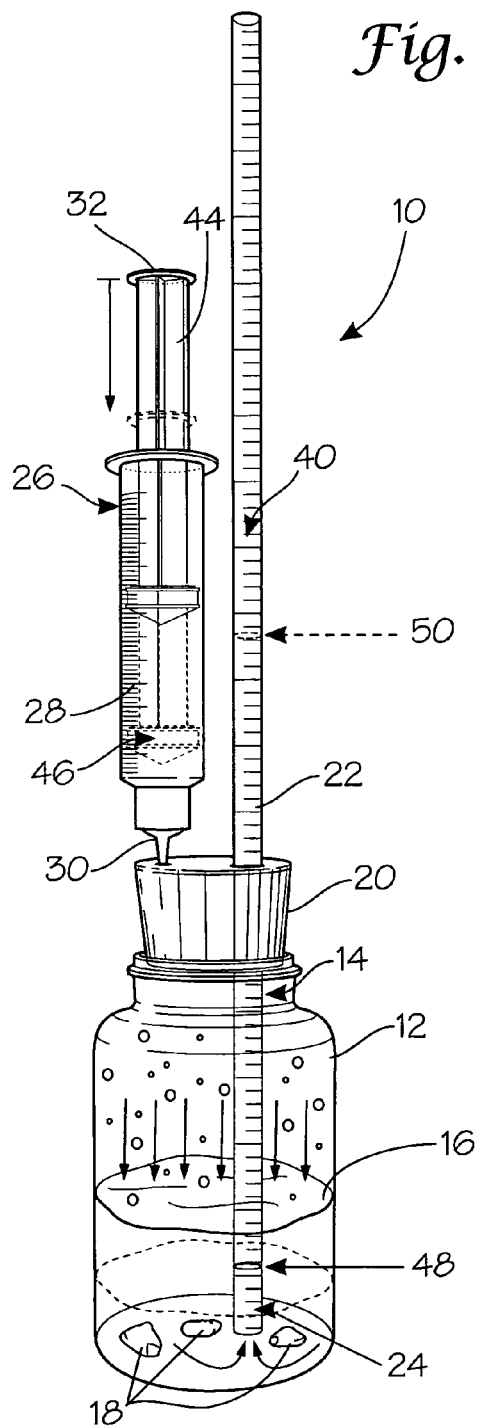
FIG. 1 shows a perspective view of the manometer according to the present invention.
Figure 2:
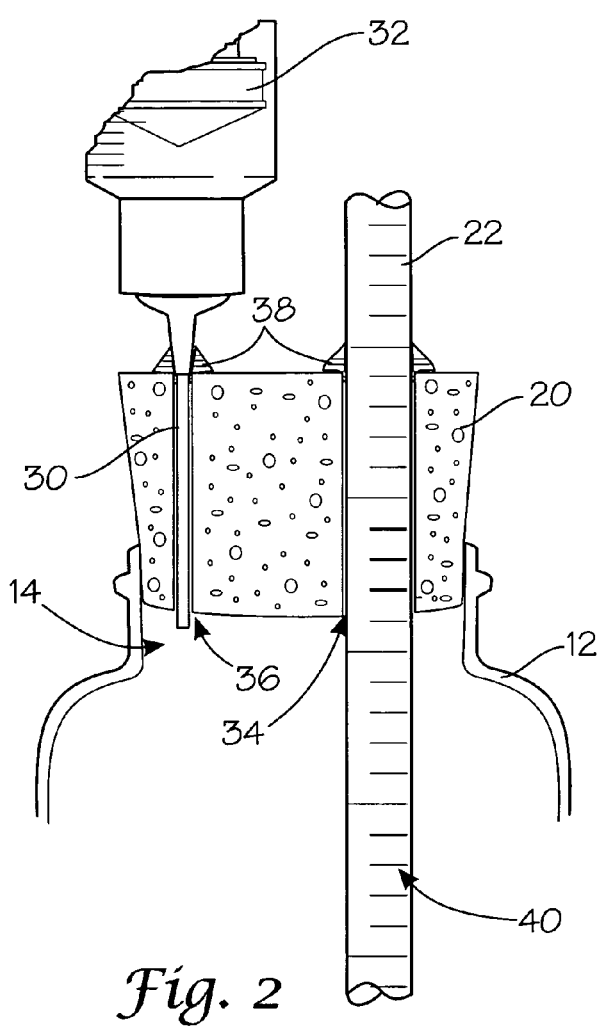
FIG. 2 shows a cross section view of the removable stopper carrying the controller and tube according to the present invention; and, FIG. 3 shows a stand for holding a pair of manometers according to the present invention.

With reference to the drawings, the invention will now be described in more detail. Referring to FIGS. 1 and 2, an example of a manometer apparatus for measuring gas exchange is illustrated and indicated generally by reference number 10. The illustrated example of manometer 10 includes a container 12. Container 12 is further illustrated as having a port, designated generally as 14. A liquid medium 16 and a reactant 18 are placed in container 12 through port 14. The liquid medium and reactant interact with each other to produce a change in gas levels within the container by either producing gas or absorbing gas. For illustrative purposes, liquid medium 16 may comprise a peroxide, such as hydrogen peroxide, and reactant 18 may by essentially anything that reacts with the peroxide, such as soil, seeds, salts, food stuffs like oatmeal, and living tissue which reacts with the peroxide.

In a further embodiment, container 12 comprises a bottle, flask, beaker, test tube, and the like, composed of polymeric plastic or glass, for example. Use of polymeric plastic provides excellent durability, especially for classroom environments where accidents are bound to occur, but does have a slight tendency to absorb some gases. Other materials well known to those skilled in the art may also be used and it is not essential that only polymeric plastic or glass be used for container 12 to practice the invention.

A removable stopper 20 is provided for insertion into port 14 to create an airtight seal between stopper 20 and the insides of port 14 of container 12. Further, port 14 of container 12 includes a narrowed neck portion having a constant diameter for receiving stopper 20. While a constant diameter for port 14 is not essential, this construction and arrangement is well adapted to receive stopper 20 to create an airtight seal, while also allowing for easy removal of the stopper to insert liquid medium 16 and reactant 18. It is also advantageous to provide a stopper 20 which is slightly tapered, as illustrated in the figures, which allows the stopper to act as a wedge and fit tightly into port 14 to create an airtight seal.

In a further embodiment, container 12 has approximately a 200 cc capacity for receiving liquid medium 16. This is a sufficient capacity for measuring numerous vigorous reactions that could be conducted in a typical hour long classroom setting. However, the invention is not limited to such a capacity as both larger and smaller sizes of containers may be used to practice the invention.

A tube 22 is provided extending through the stopper into the container having a distal end, designated generally as 24, for being submerged in liquid medium 16. Tube 22 is adapted for receiving liquid medium 16 and monitoring a change in the level of the liquid medium within container 12 as a result of gas exchange. Gas exchange is defined herein as both the production and/or absorption of gas which produces a differential pressure affect on liquid medium 16, causing the liquid medium to rise or fall within container 12. In a further embodiment, the distal end of the tube is positioned approximately ½ cm from a bottom of the container, and the container is adapted for submerging the distal end of the tube in at least 1 cm of liquid medium.

A controller, designated generally as 26, is provided extending through stopper 20 into container 12 for setting liquid medium 16 at a level within tube 22. Accordingly, controller 26 is operable to direct liquid medium 16 into tube 22 to a desired level so that a change in gas levels caused by the interaction of reactant 18 with liquid medium 16 can be monitored through a change in the level of liquid medium 16 within tube 22 by observing the level in tube 22 against graduated markings on the tube or on a backing adjacent the tube. Alternatively, controller 26 may be operated to withdraw gas in container 12, which in turn causes the liquid in tube 22 to draw down at the start of an experiment. This is done at the start of an experiment to "zero out" the apparatus in both the testing container and the control container, as is discussed in further detail herein below, so that the level of liquid medium in tube 22 of the testing and control containers are at the same level.

In a further embodiment, controller 26 includes a graduated reservoir 28 mounted outside container 12. In a further embodiment, the graduated reservoir has approximately a 10 cc to 25 cc capacity for containing a fluid medium. The fluid medium may be either a gas or liquid, but is preferably a gas. For hydrogen peroxide reactions, controller 26 contains air at the outset, but for special manometric conditions, the controller may be employed as a liquid reservoir to add liquid to container 12. By locating controller 26 in stopper 20, the need for various connection tubes as is typically found in other manometers is eliminated. A conduit 30 is also included in controller 26 which extends through stopper 20 in an airtight arrangement into container 12 to interconnect graduated reservoir 28 and container 12 in fluid communication. Fluid communication is defined a continuous passage between graduated reservoir 28 and the interior of container 12, and is not limited to the transfer of liquid or gas between the graduated reservoir and the container. A movable plunger 32 is mounted in graduated reservoir 28 in a tight fitting manner.

Referring to FIG. 1, plunger 32 has a withdrawn position, designated generally as 44 and shown in solid lines, which creates space in graduated reservoir 28 to hold a fluid medium, gas or liquid. For example, in a preferred embodiment, graduated reservoir 28 holds ambient air. Plunger 32 may also be moved to a depressed position, designated generally as 46 and shown in dotted lines, which forces the fluid medium, which is air in the example noted above, to be injected into container 12, increasing the amount of air on top of liquid medium 16 in container 12, which increases pressure on the liquid medium and forces it up tube 22. Alternatively, as noted above, plunger 32 may be withdrawn to draw gas out of container 12. The controller is not employed to draw liquid out of container 12 into the graduated reservoir as conduit 30 is not submerged in the liquid medium and as illustrated best in FIG. 2, conduit 30 only slight protrudes into container 12. In fact, it is not necessary for conduit 30 to even enter the space contained within container 12 at all. Accordingly, movement of plunger 32 results in a change in the level of liquid medium 16 in container 12 by adding additional gas or liquid to affect the differential pressure within container 12. This further forces liquid medium 16 upward or downward in tube 22. For example, when starting an experiment, plunger 32 is depressed to force gas from graduated reservoir 28 into container 12. This forces liquid medium 16 into tube 22 from a starting point, designated generally as 48, in distal end 24 of tube 22 upward to a desired set point, designated generally as 50 and indicated in dotted line form. The level of liquid medium 16 in tube 22 can be set at any point within the tube by depressing or withdrawing the plunger. To more easily monitor the level of liquid medium within tube 22, it is preferable to depress plunger 32 until the liquid medium rises above stopper 20. As the interaction between liquid medium 16 and reactant 18 progresses, the level of liquid medium in tube 22 will rise or fall depending on gas production or uptake which affects the pressure differential within container 12. Further, operation of plunger 32 between depressed and withdrawn positions allows the level of liquid medium in tube 22 to be adjusted and reset during a testing procedure without exposing an interior of the container to ambient air. This is particularly useful when radioactive isotopes are involved in the reactions as they are prevented from escaping container 12 and the manometer can still be adjusted without exposing the interior of container 12 to ambient air and the user to radioactive particles.

Referring to FIG. 2, in a further embodiment, removable stopper 20 comprises a solid rubber stopper which includes a first hole, designated generally as 34, extending through the stopper for receiving tube 22 in an airtight arrangement, and a second hole, designated generally as 36, extending through the stopper for receiving controller 26 in an airtight arrangement. Advantageously, removable stopper 20 is a solid rubber stopper and tube 22 is tightly fitted into first hole 34 and conduit 30 of controller 26 is tightly fitted into second hole 36 to create an airtight seal. In a further embodiment, a gas impermeable sealant 38, such as epoxy, resin, and the like, may also be disposed in first hole 34 and second hole 36 for creating an airtight seal between stopper 20, tube 22, and conduit 30 of controller 26.

Also, in a further embodiment, using the example of a 200 cc capacity container noted above, port 14 is adapted to receive at least a #7 size rubber stopper well known to those skilled in the art. The #7 size rubber stopper is easily capable of carrying both tube 22 and controller 26 as required to operate the invention.

In a further embodiment, tube 22 is constructed to include graduated indicia, designated generally as 40, for gauging a change in the liquid medium level within tube 22. However, it is not essential that tube 22 be graduated as this increases the cost of the manometer. There are numerous ways to monitor the rise and fall of liquid medium within tube 22, such as simply marking on the tube and measuring the distance between markings, or providing a graduated backing, such as a ruler or lined paper mounted adjacent the tube with which to gauge changes in the level of liquid medium within tube 22. Also, in a further embodiment, tube 22 is advantageously comprised of a shatter resistant material such as acrylic and carbonate polymer, or other impact resistant plastics to prevent accidental damage during handling of the manometer. However, other durable and even breakable materials well known to those skilled in the art may alternatively be used to practice The invention and the invention is not limited to being practiced with a specific type of material. In a further embodiment, tube 22 is approximately 44 cm to 56 cm in length with an external diameter of approximately ¼" to 5/16" for receiving the liquid medium. This provides a tube of sufficient volume to allow for considerable gas production to force liquid medium upward into tube 22.

In a further embodiment, a stand 42 is included which is adapted for holding the manometer in a generally upright orientation. Stand 42 may include a graduated backing, designated generally as 43, parallel with tube 22 for gauging a change in the level of liquid medium 16 within the tube 22, which eliminates any need to include graduated markings directly on tube 22. Stand 42 is not a necessary component of the invention, but is useful in practice when operating dual manometers as is discussed below.

Figure 3:
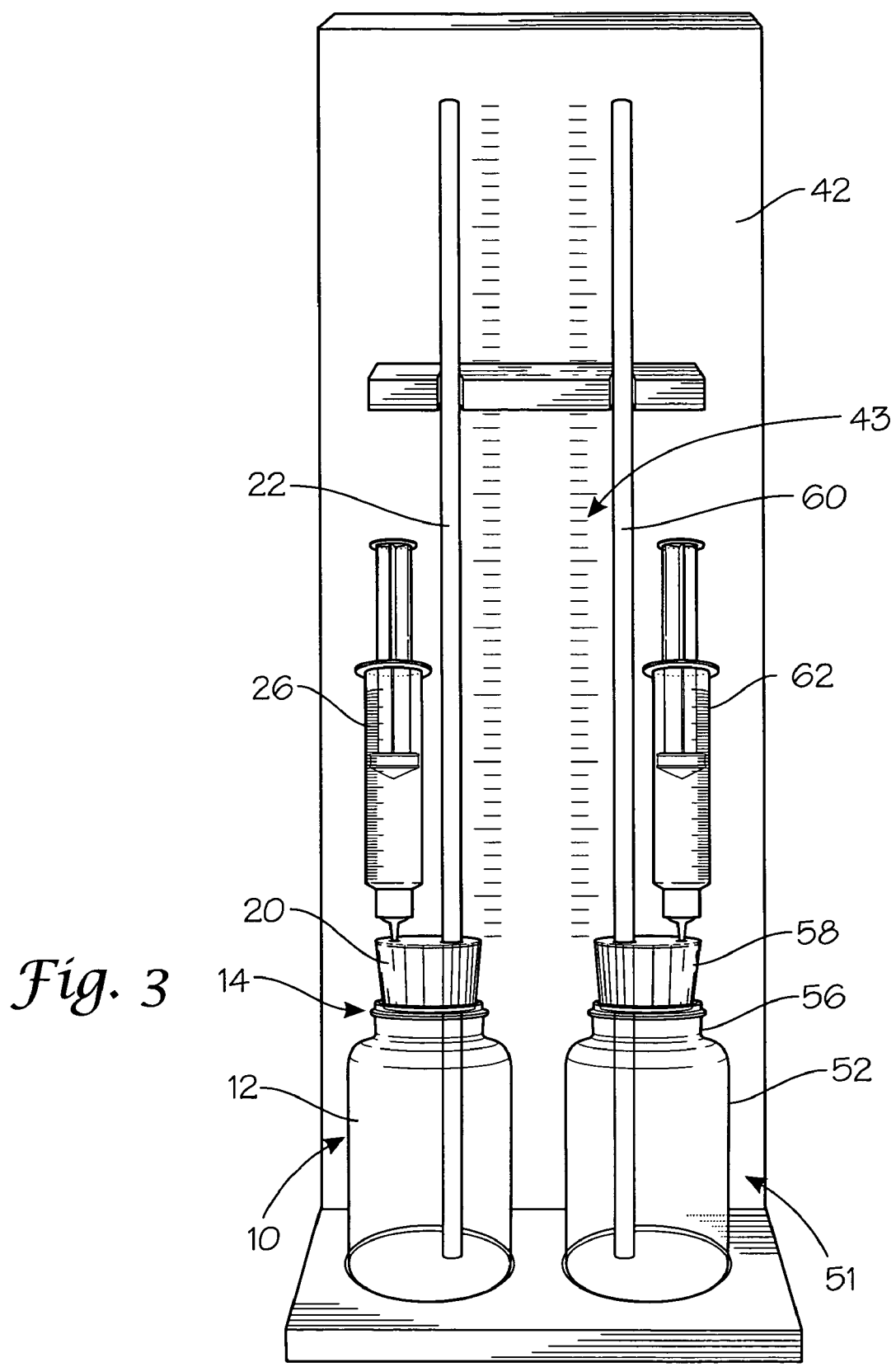

Referring to FIG. 3, a method for measuring gas exchange is also disclosed herein based upon the above understanding of the construction and arrangement of the manometer. The method involves providing a first manometer, designated generally as 10, to function as a testing manometer as described above, and a second manometer to function as a control manometer, designated generally as 51, for monitoring the effect of temperature changes. Accordingly, the method includes providing a container 12 having an open port 14 for accessing the container. Liquid medium 16 is inserted into container 12. Reactant 18 is inserted into container 12 for interacting with liquid medium 16 to produce a change in gas levels within container 12. Removable stopper 20 is provided carrying elongated tube 22 and controller 26 for insertion into port 14, creating an airtight seal. Stopper 20 carrying tube 22 and controller 26 is inserted into port 14 so that distal end 24 of tube 22 is submerged in liquid medium 16 and controller 26 is in fluid communication with container 12. As noted above, it is advantageous to position distal end 24 of tube 22 at ½ cm from the bottom of container 12 to promote directing liquid medium 16 upward into tube 22. Next, controller 26 is operated to direct liquid medium 16 into tube 22 to set the liquid medium at a desired level within tube 22 so that a change in gas levels within container 12 caused by the interaction of the reactant with the liquid medium results in a change in the liquid medium level within the tube to indicate gas exchange.

In a further embodiment, the method also includes the steps of providing a control container 52. Control container 52 is a second manometer that operates as a control to account for expansion and contraction of gas due to temperature change and is identical in construction to the one described above. It includes an open port 56 for inserting a control medium into the container, a second stopper 58 carrying an elongated tube 60 and a controller 62 with the distal end of tube 60 submerged in the control medium and controller 62 in fluid communication with control container 52.

The control medium is likely to be water or another liquid sensitive to temperature and pressure change. The control medium may even be the same as liquid medium 16 but no reactant will be added to control container 52. The method includes the step of bringing both the liquid medium and the control medium into equilibrium with room temperature before running any experiments.

Controller 62 of control container 52 is operated to direct the control medium into tube 60 to set the control medium at a desired level within the tube so that a change in room temperature results in a change in the level of control medium within the tube of the control container, whereby a change in room temperature can be accounted for in accurately measuring gas exchange between liquid medium 16 and reactant 18. To account for a change in room temperature, if the control medium rises in tube 60 of control manometer 51, then temperature of the room increased during testing and gases in the room expanded. This value of the change in the level of the control medium in control manometer 51 must be deducted from the increase in the level of liquid medium in tube 22 of testing manometer 10. If the control manometer reading goes down, then the room was cooling and the amount the control medium dropped in tube 60 must be added to the values of the testing manometer.

EXAMPLE 1

Hydrogen Peroxide Seed Reaction:

To the container of both the testing manometer and the control manometer was added 40 ml. of 2% hydrogen peroxide in water. This was allowed to come to equilibrium with the surrounding air temperature at 23° C. Ten undamaged dry corn seeds, variety P3085, were then added to container 12 of the testing manometer. Both testing container 12 and control container 52 were then closed with the stoppers containing the riser tubes and controllers. The liquid level in tubes 22 and 60 were set with the respective controller and the settings recorded at the outset against a graduated chart behind and adjacent each tube. The starting level in testing container 12 was 13.1 scale units and at the end of a 15 minute run the reading was 29.5 scale units. The relative amount of gas produced (oxygen) was noted as 29.5–13.1 or 16.4 units on a graduated scale placed adjacent to the tube. During this period, the change in liquid level in tube 60 of the control manometer was ±0.7 units, thus the 16.4 test run unit value was reduced by 0.7 units to adjust for increased room temperature conditions during the test run. The adjusted unit value was 15.7 units at 23° C. In this first trial 3.89 grams of dry seed were employed as the reactant as determined using a Metier electronic balance. Thus the gas units per gram dry seed were determined as 4.03 units per gram at 23° C. Adjustments for dissolved oxygen need not be made in this trial because the hydrogen peroxide is near saturation with oxygen and is produced at a rate which quickly exceeds the amount which may dissolve in the liquid medium.

A second trial was run conducted with 3.55 grams of seed. The test run produced 15.5 gas units which was adjusted by 0.7 to give a net gas units change of 14.8. On a units gas per gram of seed this second run gave 4.16 units per gram. This was repeated twice more for a total of four runs. On a per gram basis the gas units per gram were determined as: sample 1, 4.03; sample 2, 4.16; sample 3, 4.00; sample 4, 4.10. The mean for four runs was 4.07 gas units per gram/15 minutes. The data showed a low variance and high reproducibility attesting to the utility of the manometer.

In a further embodiment, a small container such as a small test tube or small bottle may be placed in container 12. The small container can be used to hold potassium or sodium hydroxide, which will allow the manometer to run without carbon dioxide gas accumulation. In the case of corn seeds discussed above, the amount of carbon dioxide produced by respiration and oxygen employed by metabolism is a ratio of 1, thus they do not interfere with measuring oxygen released from the hydrogen peroxide as caused by corn seed catalase.

While a preferred embodiment of the invention has been described using specific terms, such description is for illustrative purposes only, and it is to be understood that changes and variations may be made without departing from the spirit or scope of the following claims.

What is claimed is:

1. A high precision low cost manometer for measuring gas exchange comprising:
a container having a port for holding a liquid medium and a reactant that interacts with said liquid medium to produce a change in gas levels within said container;
a removable stopper for insertion into said port creating an airtight seal;
a tube extending through said stopper into said container having a distal end for being submerged in said liquid medium; said tube adapted for receiving said liquid medium and monitoring a change in the level of said liquid medium within said container as a result of gas exchange;
a controller extending through said stopper into said container for setting said liquid medium at a level within said tube; and,
wherein said controller is operable to direct the liquid medium into said tube to a desired level so that a change in gas levels caused by the interaction of said reactant with said liquid medium can be monitored through a change in the level of the liquid medium within said tube.

2. The apparatus of claim 1 wherein said container comprises a bottle composed of material selected from the group consisting of polymeric plastic and glass, and wherein said container includes a narrowed neck portion having a constant diameter forming said port.

3. The apparatus of claim 1 wherein said container comprises a bottle having approximately a 200 cc capacity for receiving said liquid medium, and a port adapted to receive at least a #7 size rubber stopper.

4. The apparatus of claim 1 wherein said removable stopper comprises a solid rubber stopper.

5. The apparatus of claim 4 wherein said rubber stopper includes a first hole extending through said stopper for receiving said tube in an airtight arrangement, and a second hole extending through said stopper for receiving said controller in an airtight arrangement.

6. The apparatus of claim 5 including a gas impermeable sealant disposed in said first hole and said second hole for creating an airtight seal between said stopper, said tube, and said controller.

7. The apparatus of claim 1 wherein said tube includes graduated indicia for gauging a change in the liquid medium level within said tube.

8. The apparatus of claim 1 wherein said tube is comprised of a shatter resistant material selected from the group consisting of acrylic and carbonate polymer.

9. The apparatus of claim 1 wherein said tube is approximately 44 cm to 56 cm in length with an external diameter of approximately ¼" to 5/16" for receiving said liquid medium.

10. The apparatus of claim 1 wherein said distal end of said tube is positioned approximately ½ cm from a bottom of said container, and said container is adapted for submerging said distal end of said tube in at least 1 cm of liquid medium.

11. The apparatus of claim 1 including a stand adapted for holding said manometer in a generally upright orientation and having a graduated backing parallel with said tube for gauging a change in the level of said liquid medium within said tube.

12. The apparatus of claim 1 wherein said controller includes a graduated reservoir mounted outside said container, a conduit passing through said stopper in an airtight arrangement into said container to interconnect said graduated reservoir and container in fluid communication, and a movable plunger mounted in said graduated reservoir, whereby movement of said plunger forces a fluid medium to be injected into said container or withdrawn into said graduated reservoir to result in a change in said level of liquid medium in said container and thereby the level of liquid medium in said tube, which allows the level of liquid medium in said tube to be adjusted and reset during a testing procedure without exposing an interior of said container to ambient air.

13. The apparatus of claim 12 wherein said graduated reservoir has approximately a 10 cc to 25 cc capacity for containing said fluid medium.

14. The apparatus of claim 1 wherein said liquid medium comprises peroxide.

15. The apparatus of claim 1 wherein said reactant is selected from the group consisting of soil, seeds, salts, food stuffs, and living tissue which reacts with the liquid medium.

16. A method for measuring gas exchange comprising the steps of:
providing a container having an open port for accessing said container;
inserting a liquid medium into said container;
inserting a reactant into said container for interacting with said liquid medium to produce a change in gas levels within said container;
providing a removable stopper carrying an elongated tube and a controller for insertion into said port creating an airtight seal;
inserting said stopper carrying said tube and said controller into said port so that a distal end of said tube is submerged in said liquid medium and said controller is in fluid communication with said container; and,
operating said controller to direct said liquid medium into said tube to set the liquid medium at a desired level within said tube so that a change in gas levels within said container caused by the interaction of said reactant with said liquid medium results in a change in the liquid medium level within said tube to indicate gas exchange.

17. The method of claim 16 including the steps of providing a control container having an open port and inserting a control medium into said container.

18. The method of claim 17 including the step of bringing both said liquid medium and said control medium into equilibrium with room temperature.

19. The method of claim 17 including the steps of providing a second stopper carrying an elongated tube and a controller, and inserting said second stopper into said port of said control container in an airtight arrangement so that a distal end of said tube is submerged in said control medium and said controller is in fluid communication with said control container.

20. The method of claim 19 including the step of operating said controller of said control container to direct said control medium into said tube to set the control medium at a desired level within said tube so that a change in room temperature results in a change in the level of control medium within said tube of said control container, whereby a change in room temperature can be accounted for in accurately measuring gas exchange between said liquid medium and said reactant.

21. An apparatus for measuring gas exchange comprising:
- a stopper for use with a container having a liquid medium and a reactant for creating gas exchange, said stopper being adapted to be removably inserted into a port of said container to create an airtight seal with said container;
- a tube carried by said stopper for extending into said container to receive said liquid medium and monitor a change in the level of said liquid medium within said container as a result of gas exchange when said stopper is inserted into said port; and,
- a controller carried by said stopper for extending into said container to set the level of said liquid medium within said tube when said stopper is inserted into said port, and allowing for the level of said liquid medium within said tube to be reset without exposing an interior of said container to ambient air so that a change in gas levels within said container can be monitored.

22. The apparatus of claim 21 wherein said stopper comprises a solid rubber stopper having a first hole extending through said stopper for receiving said tube in an airtight arrangement, and a second hole extending through said stopper for receiving said controller in an airtight arrangement.

23. The apparatus of claim 22 including a gas impermeable sealant disposed in said first hole and said second hole for creating an airtight seal between said stopper, said tube, and said controller.

24. The apparatus of claim 21 wherein said controller includes a graduated reservoir mounted outside said container, a conduit passing through said stopper in an airtight arrangement into said container to interconnect said graduated reservoir and container in fluid communication, and a movable plunger mounted in said graduated reservoir, whereby movement of said plunger forces a fluid medium to be injected into said container or withdrawn into said graduated reservoir to result in a change in said level of liquid medium in said container and thereby the level of liquid medium in said tube.

* * * * *